United States Patent [19]

Felix

[11] Patent Number: 4,724,261
[45] Date of Patent: Feb. 9, 1988

[54] CYCLIC UREAS

[75] Inventor: Raymond A. Felix, Richmond, Calif.

[73] Assignee: Stauffer Chemical Company, Westport, Conn.

[21] Appl. No.: 933,833

[22] Filed: Nov. 24, 1986

[51] Int. Cl.$^4$ ............................................ C07D 233/70
[52] U.S. Cl. .................................... 548/322; 564/305
[58] Field of Search ........................................ 548/322

[56] References Cited

U.S. PATENT DOCUMENTS 4,273,785  6/1981  Shepherd ........................ 564/305 X

OTHER PUBLICATIONS

Chemical Abstracts, 70: 19981n(1969), [Steffan, G., Chem. Ber. 1968, 101(11), 3688–95].
Chemical Abstracts, 97: 109924h(1982), [Mostamandi, A. et al., Zh. Org. Khim. 1982, 18(5), 977–80].
Hofmann, K., Imidazole and Its Derivatives, Part I, Interscience, New York, 1953, pp. 64–65 and 227.

Primary Examiner—Richard A. Schwartz
Attorney, Agent, or Firm—Paul R. Martin

[57] ABSTRACT

A process for the preparation of cyclic urea compounds in which a substituted anilino alkanone is reacted with an arylsubstituted isocyanate to form an intermediate imidazoline compound, and said imidazoline compound is hydrogenated in the presence of suitable catalyst to form an imidazolidine of the formula

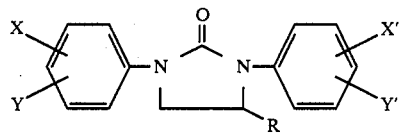

wherein X, X', Y and Y' are the same or different and are selected from the group consisting of trifluoromethyl, chloro, bromo, fluoro, hydrogen, cyano, nitro, alkyl, thioalkyl, halothioalkyl, alkoxy and sulfonylalkyl wherein the alkyl groups have from 1 to 4 carbon atoms; and R is selected from the group consisting of hydrogen and alkyl having from 1 to about 4 carbon atoms. Also included are intermediate anilino alkanones and the process of making them.

6 Claims, No Drawings

CYCLIC UREAS

BACKGROUND OF THE INVENTION

The present invention relates to a process for the preparation of certain cyclic urea compounds, which have been found to be effective herbicides.

Herbicides have been used for many years by farmers, commercial agricultural companies and other industries in order to eliminate weed pests and thereby increase crop yields of such staple crops as corn, soybeans, rice and the like.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the coil, and the post-emergence herbicides are normally applied to plant surfaces after emergence of the weeds or other unwanted plants from the soil. Some herbicides are effective both as pre- and post-emergence herbicides. The cyclic urea compounds prepared in accordance with the process of this invention fall into that category.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

DESCRIPTION OF THE INVENTION

The process of the invention is used to make cyclic urea compounds of the formula

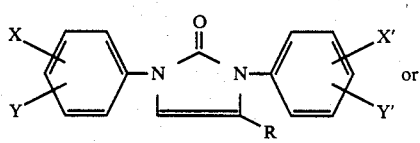 (I)

or

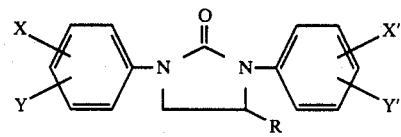 (II)

in which

X, X', Y and Y' are the same or different and are selected from the group consisting of trifluoromethyl, chloro, bromo, fluoro, hydrogen, cyano, nitro, alkyl, thioalkyl, halothioalkyl, alkoxy and sulfonylalkyl wherein the alkyl groups have from 1 to 4 carbon atoms; and R is selected from the group consisting of hydrogen and alkyl wherein the alkyl groups have from 1 to 4 carbon atoms.

The foregoing cyclic urea compounds can prepared in accordance with the process of this invention which comprises:

(a) reacting an aryl substituted anilino alkanone having the formula

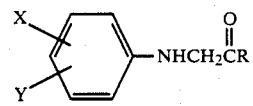

with an aryl substituted isocyanate of the formula

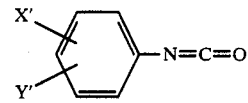

to form an intermediate imidazoline of the formula

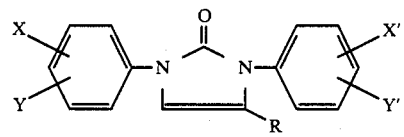

and (b) hydrogenating said intermediate imidazoline in the presence of a suitable catalyst to form the end product, an imidazolidine having the formula

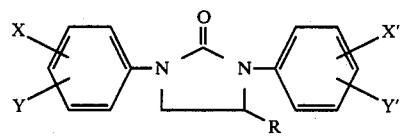

wherein

X, X', Y and Y' are the same or different and are selected from the group consisting of trifluoromethyl, chloro, bromo, fluoro, hydrogen, cyano, nitro, alkyl, thioalkyl, halothioalkyl, alkoxy and sulfonylalkyl wherein the alkyl groups have from 1 to 4 carbon atoms; and R is selected from the group consisting of hydrogen and alkyl wherein the alkyl groups have from 1 to about 4 carbon atoms.

This reaction can be represented schematically as follows:

1.

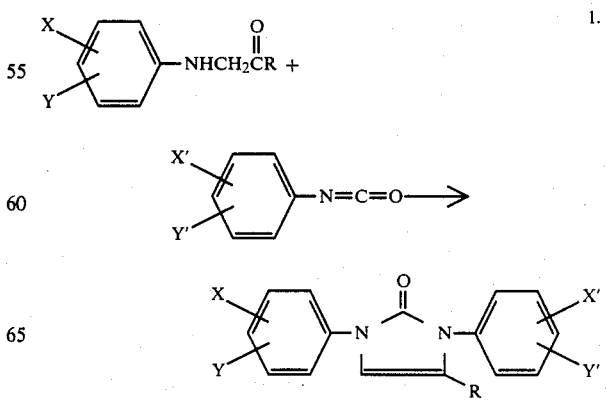

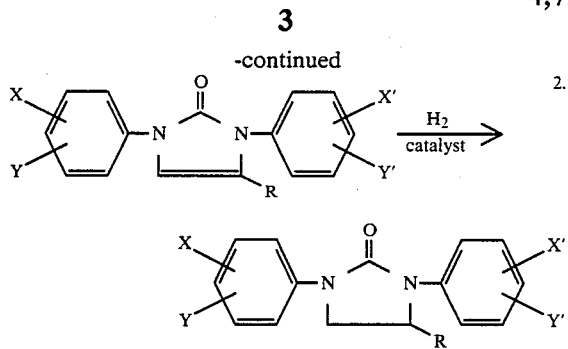

wherein X, X', Y, Y' and R are as defined above.

As used herein, the term "cyclic urea" encompasses the imidazoline compounds produced by the reaction of the aryl substituted anilino alkanones with the aryl substituted isocyanates in step (a) of the process of the invention, and also the imidazolidines produced as a consequence of the hydrogenation of the intermediate imidazolines in step (b) of the process of the invention.

As indicated, the process is a two-step reaction, and can be terminated at the end of the first step, i.e., step (a), to isolate the imidazoline compounds which are also herbicidally active. These are new compounds and are encompassed within the scope of this invention.

Preferably, however, the reaction is continued with the hydrogenation step, i.e., step (b), to produce the most desired end products, the imidazolidine compounds.

Representative compounds which can be prepared in accordance with the process of the invention include:

1-(3-trifluoromethyl)phenyl-3-(4-fluoro)phenyl-4-ethyl imidazolidine-2-one
1-(3-trifluoromethyl)phenyl-3-(4-fluoro)phenyl-4-ethyl-4-imidazoline-2-one
1,3-bis-(3-trifluoromethyl)phenyl-4-ethyl-4-imidazoline-2-one
1,3-bis-(3-trifluoromethyl)phenyl-4-ethyl imidazolidine-2-one
1-(3-trifluoromethyl)phenyl-3-(4-bromo)phenyl-4-ethyl imidazolidine-2-one
1-(3-trifluoromethyl)phenyl-3-(2-methyl)phenyl-4-ethyl-imidazolidine-2-one
1-(3-trifluoromethyl)phenyl-3-(4-methyl)phenyl-4-ethyl imidazolidine-2-one
1-(3-trifluoromethyl)phenyl-3-(2-methyl)phenyl-4-ethyl-4-imidazoline-2-one
1-(3-trifluoromethyl)phenyl-3-(4-methyl)phenyl-4-ethyl-4-imidazoline-2-one
1-(3-trifluoromethyl)phenyl-3-(4-chloro)phenyl-4-ethyl-4-imidazoline-2-one
1-(3-trifluoromethyl)phenyl-3-(4-bromo)phenyl-4-ethyl-4-imidazoline-2-one Examples 1-3 below illustrate the conduct of the process.

Example 1 describes the preparation of the indicated imidazolidine-2-one beginning with the starting compounds, an anilino-2-butanone and para-fluorophenyl isocyanate.

Example 2 describes the preparation of the indicated imidazolidine beginning with an imidazoline-2-one starting material, which is produced in accordance with the first step of the process of the invention.

Example 3 describes the bromination of an imidazolidine-2-one, which has undergone the hydrogenation step. It has been found that when the imidazoline compound undergoes hydrogenation, the halogen substituent groups on the phenyl rings are sometimes cleaved off. The groups can be replaced, however, by simple halogenation of the imidazolidine-2-one compound realized or obtained at the end of step (2).

Suitable analytical techniques such as IR, NMR and MR were used to identify the products.

EXAMPLE 1

Preparation of 1-(3-Trifluoromethyl)phenyl-3-(4-fluoro)phenyl-4-ethylimidazolidine-2-one 3.7 Grams (g) (0.016 mole) of 1-(3-trifluoromethyl)anilino-2-butanone and 6 milliliters (ml) of 4-fluorophenyl isocyanate (0.053 mole) were combined and heated neat on a steam bath (100° C.) for one hour. The product was extracted with ether, washed with water, dried over magnesium sulfate and stripped to dryness on a rotary evaporator. The resulting material was then extracted with ether and put through an alumina column with ether to yield 4.1 g of 1-(3-trifluoromethyl)phenyl-3-(4-fluoro)-phenyl-4-ethyl-4-imidazoline-2-one, identified by suitable analytical techniques.

Two grams of 1-(3-trifluoromethyl)phenyl-3-(4-fluoro)phenyl-4-ethyl-4-imidazoline-2-one (0.0057 mole) were then combined with 20 ml of ethanol and 0.2 g of 10% palladium on carbon. The mixture was shaken in a hydrogenation apparatus while hydrogen (H$_2$) at 50 psi was being added. After 3 hours, another 0.1 g of palladium on carbon were added. The mixture was allowed to shake another 5 hours when another 0.1 g of catalyst were added. After two more hours of shaking the reaction was 97% complete. The mixture was diluted with ether, filtered through a calcium carbonate filtering medium, washed with water and stripped to dryness in a rotary evaporator to yield 1.6 g of the subject product, identified as such by suitable analytical techniques.

EXAMPLE 2

Preparation of 1-(3-Trifluoromethyl)phenyl-3-(4-methyl)phenyl-4-ethylimidazolidine-2-one 1.8 grams (0.005 mole) of 1-(3-trifluoromethyl)phenyl-3-(4-methyl)phenyl-4-ethyl-4-imidazoline-2-one, 20 ml ethanol and 0.5 g of 10% palladium on carbon were combined and shaken in a hydrogenation apparatus with H$_2$ at 50 psi. The reactants were shaken for 45 minutes, when another 0.2 g 10% palladium on carbon was added to the bottle. The mixture was shaken another two hours and another 0.1 g of 10% palladium on carbon was again added to the hydrogenation bottle. The mixture was shaken another 2 hours. The product was filtered through a filtering medium and the ethanol layer was stripped on a rotary evaporator, diluted with ether, washed with 2N hydrochloric acid, dried over magnesium sulfate and evaporated to dryness. 1.4 grams of product were obtained which formula and structure was confirmed by infrared, nuclear magnetic resonance and mass spectroscopy.

EXAMPLE 3

Preparation of 1-(3-Trifluoromethyl)phenyl-3-(4-bromo)phenyl-4-ethylimidazolidine-2-one 1.4 Grams (0.004 mole) of 1-(3-trifluoromethyl)phenyl-3-phenyl-4-ethylimidazolidine-2-one and 15 ml of acetic acid were combined in a round-bottom flask fitted with a magnet. The mixture was stirred in a water bath and bromine (0.004 mole) was gradually added. After the bromine addition, the mixture was allowed to stir for two hours. The mixture was extracted with ether, washed with water and 1N sodium bicarbonate, then again with water. The product was dried over magnesium sulfate, and the ether layer evaporated to dryness. 1.1 Grams of product was obtained, which infrared, nuclear magnetic resonance and mass spectroscopy confirmed to be the subject compound.

Compounds which have been prepared in accordance with the same general techniques of Examples 1-3 above are set forth in Table I below.

TABLE 1

Imidazolidine-2-ones

| Cmpd. No. | X | Y | X' | Y' | R | Physical Constant |
|---|---|---|---|---|---|---|
| 1 | H | 3-$CF_3$ | H | 4-F | $C_2H_5$ | m.p. 74–78° C. |
| 2 | H | 3-$CF_3$ | 3-$CF_3$ | H | $C_2H_5$ | m.p. 112–116° C. |
| 3 | H | 3-$CF_3$ | H | 4-Br | $C_2H_5$ | m.p. 100–106° C. |
| 4 | H | 3-$CF_3$ | H | 2-$CH_3$ | $C_2H_5$ | semi-solid |
| 5 | H | 3-$CF_3$ | H | 4-$CH_3$ | $C_2H_5$ | m.p. 105–106° C. |
| 6 | H | 3-$CF_3$ | H | H | $C_2H_5$ | m.p. 77–79° C. |

TABLE 2

Imidazoline-2-ones

| Cmpd. No. | X | Y | X' | Y' | R | Physical m.p. °C. |
|---|---|---|---|---|---|---|
| 7 | H | 3-$CF_3$ | H | 4-F | $C_2H_5$ | 96–98 |
| 8 | H | 3-$CF_3$ | H | 3-$CF_3$ | $C_2H_5$ | 88–96 |
| 9 | H | 3-$CF_3$ | H | 4-C≡N | $C_2H_5$ | 110–112 |
| 10 | H | 3-$CF_3$ | H | 3-Cl | $C_2H_5$ | 87–89 |
| 11 | H | 3-$CF_3$ | H | 2-$CH_3$ | $C_2H_5$ | 80–86 |
| 12 | H | 3-$CF_3$ | H | 4-$CH_3$ | $C_2H_5$ | 114–116 |
| 13 | H | 3-$CF_3$ | H | 4-Cl | $C_2H_5$ | 129–130 |
| 14 | H | 3-$CF_3$ | 3-Cl | 4-Cl | $C_2H_5$ | 93–94 |
| 15 | H | 3-$CF_3$ | H | 4-Br | $C_2H_5$ | 122–125 |

In carrying out the process of this invention, the reaction of the alkanone and the isocyanate is preferably conducted at atmospheric pressure and at temperatures of from 0° to 150° C., preferably at 90°–100° C. An excess of isocyanate is preferred to consume the water produced in the cyclization step.

No solvent is needed. However, solvents non-reactive to the intermediates can be used.

In general step (a) of the reaction can be substantially completed within about 2 hours reaction time, preferably one hour; however, the completion time may vary depending on the starting intermediates.

The hydrogenation step in the process of the invention is conventionally carried out in a hydrogenation which can be used to introduce hydrogen at about 50 psi into the reaction mixture. Any other means of accomplishing hydrogenation would be acceptable.

The catalyst used during the hydrogenation step can be any conventional catalyst as known to those skilled in the art; however, the preferred catalyst is palladium on carbon. Other suitable catalysts would include platinum oxide, platinum on carbon, and various palladium and platinum compounds.

The isocyanate compounds which are used as the primary reactants in the first step of the invention are commercially available or can be prepared by known literature procedures. The preferred isocyanate is a substituted phenyl isocyanate.

The anilino alkanones which are used as one of the primary reactants in the first step of the invention can be prepared by reacting an aryl substituted anilino alcohol having the formula

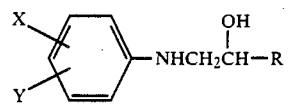

with di-t-butyl dicarbonate to form a compound having the formula

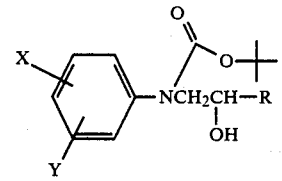

This product is further reacted with sodium hypochlorite in the presence of a phase transfer catalyst to form a compound having the formula

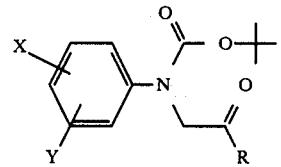

which is then treated with hydrogen chloride gas to yield a compound having the formula

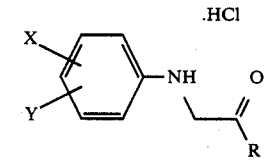

The latter in turn is then treated with a base to yield a compound having the formula

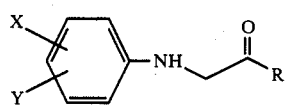

wherein X, Y and R are as previously defined.

The anilino alkanones are novel compounds, as well as the process of making them.

Example 4 below illustrates the preparation of a preferred compound.

EXAMPLE 4

Preparation of 1-(3-Trifluoromethyl)anilino-2-butanone

In a 250 ml flask was placed 11.6 g (0.05 mole) of 1-(3-trifluoromethyl)anilino-2-butanol and 10.9 g (0.05 mole) of di-t-butyl dicarbonate. This mixture was heated 2 hours neat on a steam bath. A standard water and ether work-up yielded 15.3 g of the intermediate, N-(t-Butyl)carboxy-1-(3-trifluoromethyl)anilino-2-butanol, identified by standard analytical techniques.

In a 300 ml flask was placed 7.8 g of N-(t-butyl)carboxy-1-(3-trifluoromethyl)anilino-2-butanol, 25 ml of ethyl acetate and 1 g of tetrabutylphosphonium bromide, a phase transfer catalyst. To this stirred mixture was added 120 ml of 5% sodium hypochlorite (bleach). This mixture was stirred 1 hour and 0.5 g more catalyst an 60 ml of bleach were added. The mixture was stirred 0.5 hour longer and worked up in the usual manner to yield 7.0 g of N-(t-butyl)carboxy-1-(3-trifluoromethyl)anilino-2-butanone, identified by standard analytical techniques.

In a 250 ml flask was placed 7.0 g (0.02 mole) of N-(t-butyl)-carboxy-1-(3-trifluoromethyl)anilino-2-butanone and 50 ml of ethyl acetate. An excess of hydrogen chloride gas was then bubbled through this solution. After stirring 0.5 hour, the solution was filtered and the solids washed with ehtyl ether, to yield 3.4 g of 1-(3-trifluoromethyl)-anilino-2-butanone hydrochloride, identified as such by standard analytical techniques.

In a 200 ml flask was placed 50 ml 1N NaHCO3 and 50 ml of ether, with stirring was added 3.4 g of 1-(3-trifluoromethyl)anilino-2-butanone hydrochloride. This mixture was stirred 1 hour and phase separated. The ether layer was dried and stripped to yield 2.3 g of 1-(3-trifluoromethyl)anilino-2-butanone, identified by NMR, IR, and MS.

In addition to the foregoing examples, the process of this invention can be used to make those imidazolidines set forth in application Ser. No. 933,834.

These imidazolidines have been found to have good herbicidal activity when applied pre- or post-emergent, and when used against grasses or broadleaf weed species.

What is claimed is:

1. An imidazolin-2-one of the formula

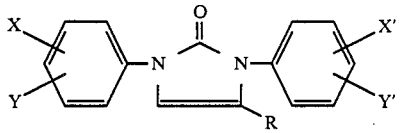

wherein
X, X', Y and Y' are the same or different and are selected from the group consisting of trifluoromethyl, chloro, bromo, fluoro, hydrogen, cyano, nitro, alkyl, thioalkyl, alkoxy and sulfonylalkyl wherein the alkyl groups have from 1 to 4 carbon atoms, and at least one of X and Y is other than hydrogen; and
R is selected from the group consisting of hydrogen and alkyl wherein the alkyl groups have from 1 to 4 carbon atoms.

2. The compound of claim 1 wherein X is hydrogen, Y is 3-trifluoromethyl, X' is hydrogen, Y' is 4-fluoro and R is ethyl.

3. The compound of claim 1 wherein X is hydrogen, Y is 3-trifluoromethyl, X' is hydrogen, Y' is 4-cyano and R is ethyl.

4. The compound of claim 1 wherein X is hydrogen, Y is 3-trifluoromethyl, X' is 3-chloro, Y' is 4-chloro and R is ethyl.

5. The compound of claim 1 wherein X is hydrogen, Y is 3-trifluoromethyl, X' is hydrogen, Y' is 4-bromo and R is ethyl.

6. The compound of claim 1 wherein X is hydrogen, Y is 3-trifluoromethyl, X' is hyrogen, Y' is 4-chloro and R is ethyl.

* * * * *